(12) United States Patent
Guenther et al.

(10) Patent No.: US 7,731,736 B2
(45) Date of Patent: Jun. 8, 2010

(54) FASTENING SYSTEM FOR SPINAL STABILIZATION SYSTEM

(75) Inventors: Kevin V. Guenther, Carver, MN (US); James R. Mujwid, Crystal, MN (US); Angela L. Hillyard, Greenfield, MN (US); Paul F. Boschert, Minneapolis, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 0 days.

(21) Appl. No.: 10/874,784

(22) Filed: Jun. 14, 2004

(65) Prior Publication Data
US 2005/0277927 A1 Dec. 15, 2005

(51) Int. Cl.
*A61B 17/70* (2006.01)
(52) U.S. Cl. .................. 606/273; 606/302; 606/265
(58) Field of Classification Search .......... 606/60, 606/72, 73, 246, 250–265, 272–273, 278, 606/286, 295–296, 319, 300, 305–308, 266, 606/301–302, 328
See application file for complete search history.

(56) References Cited

U.S. PATENT DOCUMENTS

| 225,428 | A | | 3/1882 | Graham | |
|---|---|---|---|---|---|
| 4,946,458 | A | * | 8/1990 | Harms et al. | 606/61 |
| 4,950,269 | A | * | 8/1990 | Gaines, Jr. | 606/261 |
| 5,010,879 | A | | 4/1991 | Moriya et al. | |
| 5,147,359 | A | | 9/1992 | Cozad et al. | |
| 5,181,917 | A | | 1/1993 | Rogozinski | |
| 5,201,734 | A | | 4/1993 | Cozad et al. | |
| 5,207,678 | A | | 5/1993 | Harms et al. | |
| 5,437,669 | A | * | 8/1995 | Yuan et al. | 606/61 |
| 5,545,165 | A | | 8/1996 | Biedermann et al. | |
| 5,628,740 | A | | 5/1997 | Mullane | |
| 5,683,392 | A | | 11/1997 | Richelsoph et al. | |
| 5,725,527 | A | | 3/1998 | Biedermann et al. | |
| 5,728,098 | A | * | 3/1998 | Sherman et al. | 606/61 |
| 5,782,833 | A | | 7/1998 | Haider | |
| 5,876,459 | A | | 3/1999 | Powell | |

(Continued)

FOREIGN PATENT DOCUMENTS

DE 30 32 237 A 1 3/1982

(Continued)

OTHER PUBLICATIONS

Translation of FR2780269, Dec. 31, 1999, Senegas et al. "Spinal Implant".*

(Continued)

*Primary Examiner*—Thomas C Barrett
*Assistant Examiner*—James L. Swiger
(74) *Attorney, Agent, or Firm*—Crompton, Seager & Tufte, LLC

(57) ABSTRACT

Bone fixation systems for stabilizing bones such as vertebral bodies are disclosed. The fixation systems include fixation connectors that preferably are equipped with bone anchors (e.g., screws, hooks, pins or like structures) for securing the fixation connectors to bones desired to be stabilized. The fixation systems also include linking elements (e.g., rods, plates or other members) for linking the fixation connectors together to form a stabilizing construct capable of maintaining a desired spacial relationship between bones desired to be stabilized.

13 Claims, 14 Drawing Sheets

U.S. PATENT DOCUMENTS

| | | | |
|---|---|---|---|
| 5,879,350 A | 3/1999 | Sherman et al. | |
| 5,954,725 A | 9/1999 | Sherman et al. | |
| 6,010,503 A | 1/2000 | Richelsoph et al. | |
| 6,050,997 A | 4/2000 | Mullane | |
| 6,162,234 A | 12/2000 | Freedland et al. | |
| 6,273,888 B1 * | 8/2001 | Justis | 606/272 |
| 6,302,882 B1 | 10/2001 | Lin et al. | |
| 6,331,179 B1 * | 12/2001 | Freid et al. | 606/61 |
| 6,371,957 B1 * | 4/2002 | Amrein et al. | 606/61 |
| 6,451,021 B1 * | 9/2002 | Ralph et al. | 606/61 |
| 6,457,789 B2 * | 10/2002 | Hallsten | 312/333 |
| 6,485,492 B1 | 11/2002 | Halm et al. | |
| 6,485,494 B1 | 11/2002 | Haider | |
| 6,547,789 B1 * | 4/2003 | Ventre et al. | 606/61 |
| 6,554,834 B1 * | 4/2003 | Crozet et al. | 606/65 |
| 6,613,050 B1 | 9/2003 | Wagner et al. | |
| 6,626,908 B2 * | 9/2003 | Cooper et al. | 606/266 |
| 7,335,201 B2 * | 2/2008 | Doubler et al. | 606/264 |
| 2001/0053913 A1 | 12/2001 | Freedland | |
| 2002/0052603 A1 | 5/2002 | Nichols et al. | |
| 2003/0199873 A1 | 10/2003 | Richelsoph | |
| 2007/0083199 A1 | 4/2007 | Baccelli | |

FOREIGN PATENT DOCUMENTS

| | | | |
|---|---|---|---|
| FR | 2 151 475 | 4/1973 | |
| FR | 2 780 269 | 12/1999 | |
| FR | 2780269 | * 12/1999 | 17/70 |
| WO | WO 03/068086 A1 | 8/2003 | |

OTHER PUBLICATIONS

Osteotech Inc. catalog, "Strong, Simple and Low Profile," (Date: This art was known prior to filing of present U.S. Appl. No. 10/874,784.).

Surgical Dynamics catalog, "Spiral Radius 90D," Feb. 26, 2001.

DANEK Medical, Inc. catalog, "Paragon™ Posterior Spinal System," © 1993.

Osteotech Inc. online catalog "Ovation™ Polyaxial System" © 2003.

* cited by examiner

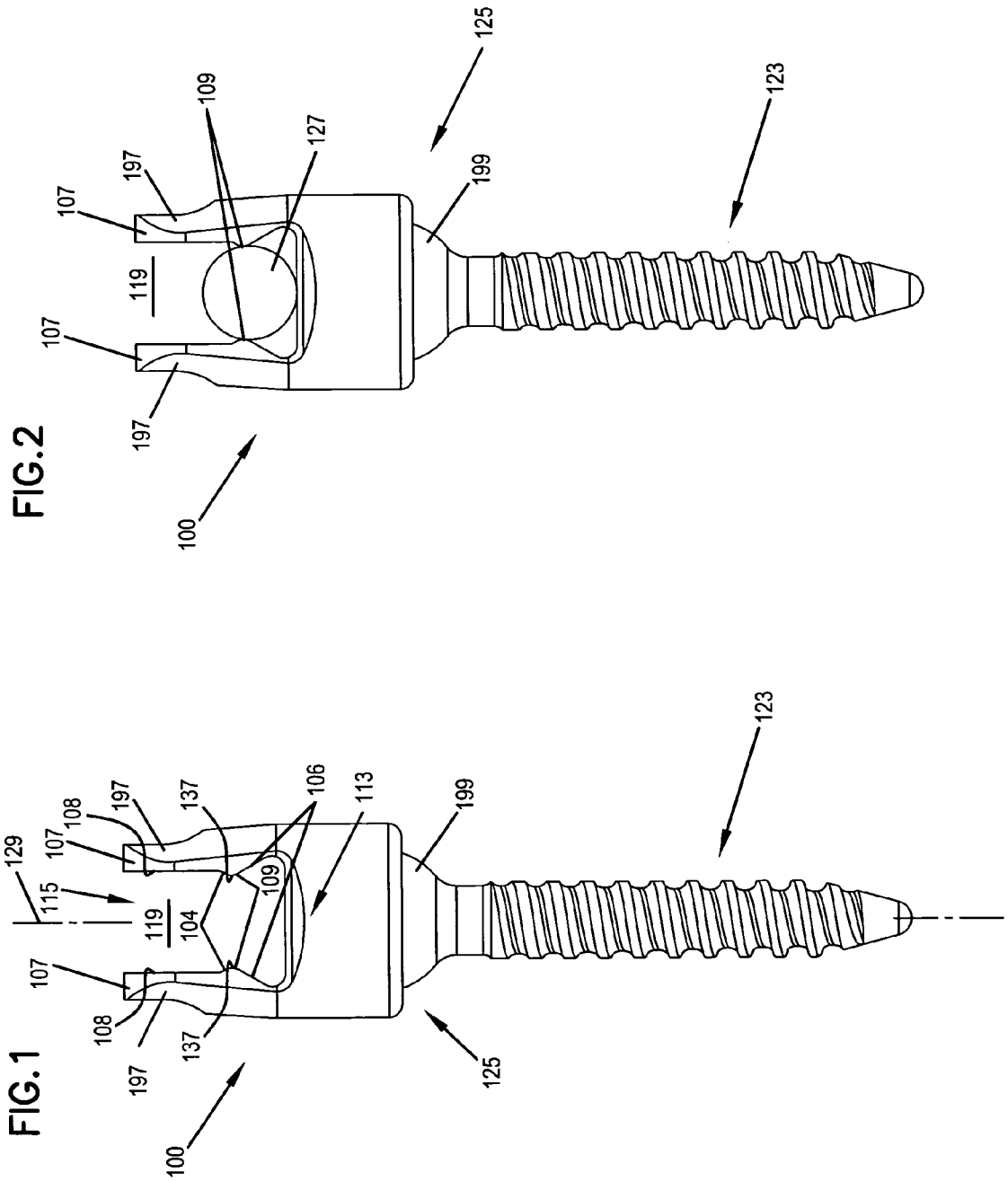

FASTENING SYSTEM FOR SPINAL STABILIZATION SYSTEM

TECHNICAL FIELD

The principles disclosed herein relate to bone stabilization systems. More specifically, the disclosure relates to intervertebral connection systems suited for stabilization of the spine.

BACKGROUND

Chronic back problems cause pain and disability for a large segment of the population. In many cases, the chronic back problems are caused by intervertebral disc disease and deterioration and loss of stability of the intervertebral joint. Examples of these spinal conditions include degenerative disc disease, scoliosis, spondylolithesis, spinal stenosis, etc. Stabilization and/or arthrodesis of the intervertebral joint can reduce the pain associated with movement of a diseased or deteriorated intervertebral joint. In order to allow for development of a solid intervertebral fusion, the spine has to be stabilized.

Spinal stabilization systems have been developed to stabilize the vertebrae to allow for fusion or stabilization of diseased intervertebral joints. One type of spinal stabilization system includes connectors and rods that are used to stabilize the spine. Some examples of such spinal stabilization systems are disclosed in U.S. Pat. Nos. 6,613,050 B1; 6,371,957 B1; 6,050,997; 5,879,350; 5,725,527; 5,628,740; 5,545,165, the entire disclosures of which are incorporated herein by reference. In these systems, connectors are anchored to the vertebral bodies desired to be stabilized by anchoring structures such as screws or hooks. One or more connecting rods are then secured to the connectors to form a connector/rod construct that stabilizes the vertebral bodies to which the connectors are secured.

In many known stabilization systems, threaded nuts are used to secure the rods to the connectors. The rods can be provisionally held in position by loosely tightening the nuts on the connectors. After desired adjustments are made with respect to the relative positioning of the bones desired to be stabilized, the nuts can be further tightened to finally secure the connector/rod construct. Typically, a torque wrench or similar device is used to achieve the required torques to finally secure the connector/rod construct. To prevent torque from being transferred to the patient while tightening the nut, an anti-torque device is frequently used in combination with the torque wrench. The effective use of the torque wrench and anti-torque device can be difficult and often is dependent upon the strength and experience of the surgeon. What are needed are alternative spine stabilization fastening techniques that do not require the use torque. What are also needed are improved means for provisional positioning of rods or other vertebrae linking elements before final tightening.

SUMMARY

One inventive aspect of the disclosure relates to spine fixation systems including structures for facilitating the provisional retention of linking elements such as rods, plates or like elements.

Another inventive aspect of the disclosure relates to spine stabilization techniques that do not require torque for final tightening.

A variety of additional inventive aspects will be set forth in the description that follows. The inventive aspects can relate to individual features and combinations of features. It is to be understood that both the foregoing general description and the following detailed description are exemplary and explanatory only and are not restrictive of the broad inventive concepts upon which the embodiments disclosed herein are based.

BRIEF DESCRIPTION OF THE DRAWINGS

FIG. 1 is a side view of a spinal fixation connector having features that are examples of inventive aspects in accordance with the principles of the present disclosure;

FIG. 2 is a side view of the spinal fixation connector of FIG. 1 with a rod provisionally retained therein;

DETAILED DESCRIPTION

Figure 3A:
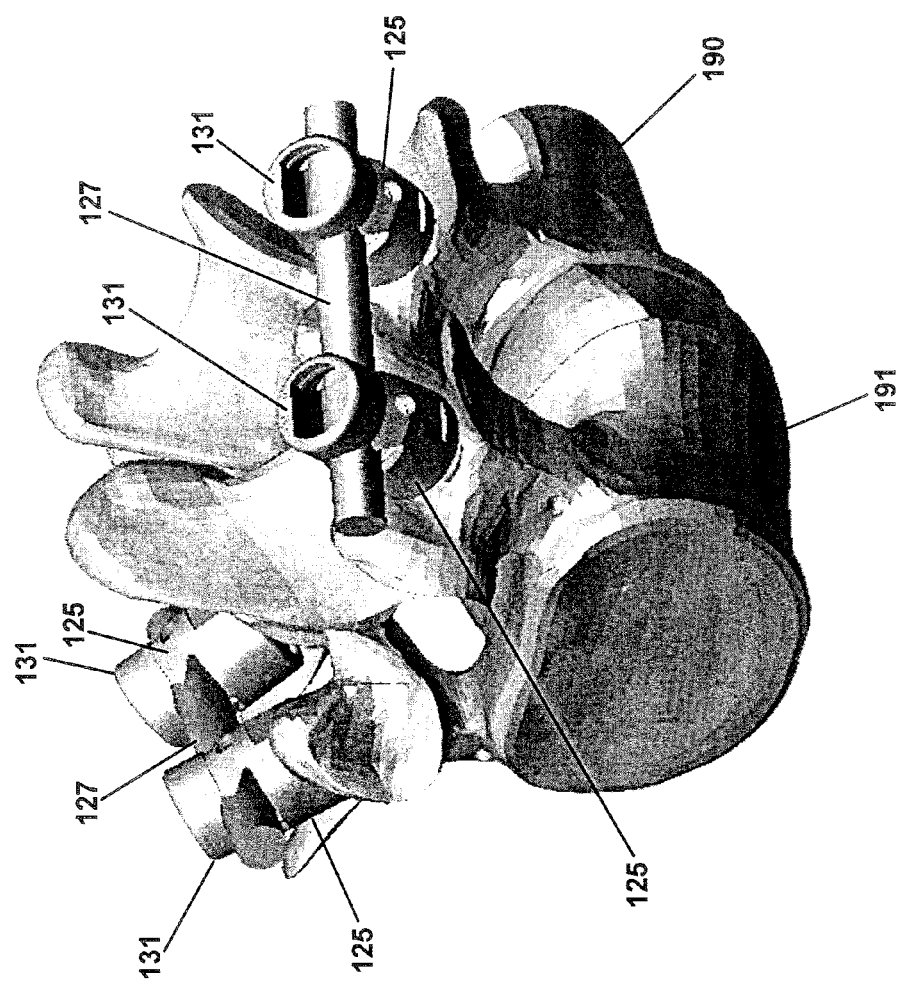
FIG. 3A is a posterior, lateral perspective view of a spine including a single level rod/connector construct which utilizes the connector of FIGS. 1 and 2.

The present disclosure relates generally to bone fixation systems for stabilizing bones such as vertebral bodies. The fixation systems include fixation connectors that preferably are equipped with bone anchors (e.g., screws, hooks, pins or like structures) for securing the fixation connectors to bones desired to be stabilized. The fixation systems also include linking elements (e.g., rods, plates or other members) for linking the fixation connectors together to form a stabilizing construct capable of maintaining a desired spacial relationship between bones desired to be stabilized.

One aspect of the present disclosure relates to bone fixation systems configured to facilitate the provisional retention of linking elements within fixation connectors. "Provisional retention" involves the temporary retention of the linking elements within the fixation connectors prior to the linking elements being finally locked relative to the fixation connectors. When a linking element is being provisionally retained, a surgeon can adjust the position or orientation of the linking element relative to the fixation connectors. Preferably, this adjustment can be achieved either manually or with mechanical advantage through the assistance of a surgical tool, without requiring loosening of any system hardware.

In certain embodiments of the present disclosure, the bone fixation system can include a receiver that automatically provisionally retains a linking element when the linking element is inserted in the receiver. For example, in one embodiment, the receiver can have a press-in-place retention arrangement for provisionally retaining the linking element. In such an embodiment, the linking element snaps or otherwise moves into a provisionally retained position when manually inserted into the receiver. In other embodiments, the fixation systems can include receivers that cooperate with secondary fastening elements (e.g., plugs, rings, sleeves or other structures) to provisionally retain linking elements at desired locations.

Another aspect of the present disclosure relates to final fastening/locking arrangements for bone fixation systems. In certain embodiments, the final fastening/locking arrangements can be finally locked without the use of torque.

FIGS. 1-3 illustrate a spinal fixation connector 125 having features that are examples of inventive aspects in accordance with the principles of the present disclosure. The fixation connector 125 includes a screw 123 for securing the connector 125 to a bone such as a vertebral body. The connector 125 also includes a receiver 100 (e.g., a saddle) coupled to the screw 123 (e.g., the screw includes a head 199 that seats at the bottom of the receiver 100). The receiver 100 includes a rod seat 113 positioned opposite from an open top end 115. The receiver 100 also includes spaced-apart legs 107 that extend upwardly from the seat 113 to the open top end 115. The legs 107 and the seat 113 cooperate to define an interior pocket 119 for receiving a rod 127 or other linking element. The legs 107 further include provisional retention structures in the form of opposing tabs 109. As described below, the tabs 109 are adapted to provisionally secure a linking element such as the rod 127 within the pocket 119.

In the depicted embodiment, the tabs 109 are integral with their corresponding legs 107 and project laterally into the pocket 119 from inner surfaces 108 of the legs 107. The tabs 109 each include an upper ramp surface 104 that faces away from the seat 113 and a lower ramp surface 106 that faces towards the seat 113. The ramp surfaces 104, 106 intersect at apexes 137 of the tabs 109.

The legs 107 also include upper portions 197 that extend upwardly from the tabs 109. The upper portions 197 can provide structure for securing a fastening element to the receiver 100 for finally locking a rod within the pocket 119 once final adjustments to the construct have been made. Such fasteners are preferably configured to force the legs 107 together such that the rod is fixedly clamped between the legs 107. Example fasteners include sleeves that mount over the exterior of the upper portions 197 of the legs 107, cross-members that extend across the top side of the pocket between the upper portions, or other structures.

To provisionally secure the rod 127 within the pocket 119 of the receiver 100, the rod 127 is inserted downwardly into the pocket 119 through the open top end 115 of the receiver 100. Prior to insertion of the rod 127, the legs 107 of the receiver 100 are in a non-deflected orientation and the distance between the apexes 137 is less than the maximum width of the rod 127 (e.g., the diameter of the rod). As the rod 127 is pressed downwardly in the pocket 119, the lower portion of the rod 127 contacts the upper ramp surfaces 104 of the tabs 109 causing the legs 107 to deflect (e.g., flex) apart to accommodate the rod. The legs 107 continue to deflect apart until the center of the rod moves below the apexes 137 of the tabs 109. Once the center of the rod 127 moves below the apexes 137, the lower ramp surfaces 106 of the tabs 109 follow the contour of the upper portion of the rod 127 such that the legs 107 begin to move inwardly back toward the non-deflected orientation. The insertion process is complete when the rod comes to rest on the seat 113 of the receiver 100 as shown in FIG. 2. As so positioned, upward movement of the rod 127 is limited or resisted by the tabs 109 (i.e., the rod 127 is captured between the tabs 109 and the seat 113). Thus, the rod 127 is provisionally retained within the pocket 119. To remove the rod 127 from the pocket 119, the rod 127 is pulled upwardly with sufficient force to cause the legs 107 to deflect back apart thereby enabling the rod to pass between the tabs 109.

In certain embodiments, the depth between the tabs 109 and the seat 113 is great enough to allow the legs to fully return to the non-deflected orientation when the rod is provisionally retained. In such embodiments, the rod can be loosely captured in the region between the tabs 109 and the seat 113. In other embodiments, the depth between the tabs 109 and the seat 113 is not great enough to allow the legs 107 to fully return to the non-deflected orientation when the rod is provisionally retained. In such embodiments, the partially deflected legs 107 apply a clamping force to the rod 127, which resists rotational movement and axial sliding of the rod relative to the receiver 100. The clamping force is applied through the tabs 109 such that the rod 127 is clamped between the tabs 109 and the seat 113. Preferably, the clamping force is sufficiently small to allow the rod to be rotated or axially slid relative to the rod either manually or with the aid of medical instrumentation.

The legs 107 of the receiver 100 can be manufactured from various materials such as, for example, Titanium, Nitinol, Stainless Steel, Thermoplastic polymers, Thermoset polymers or other materials. When the legs 107 deflect to accommodate the rod 127, the legs 107 preferably do not deform beyond the elastic limits of the material forming the legs 107. Thus, when deflected outwardly, the legs 107 are spring biased back toward the non-deflected orientation by the inherent elasticity of the material forming the legs 107.

The connection provided between the receiver 100 and the rod 127 can be referred to as a "snap-fit connection." As used herein, the phrase "snap-fit connection" means a connection provided by a member that is flexed or deflected from a retaining position to a non-retaining position, and then moves back toward the retaining position by the inherent flexibility or elasticity of the member.

In the connector 125 of FIGS. 1 and 2, the screw 123 has a poly-axial relationship relative to the receiver 100 prior to final tightening. In other embodiments, the screw can have a fixed relationship relative to the receiver. Further, while a screw 123 anchor has be depicted in FIGS. 1 and 2, other types of anchors such as hooks, rivets, pins or other structures, could also be used.

Figure 3B:
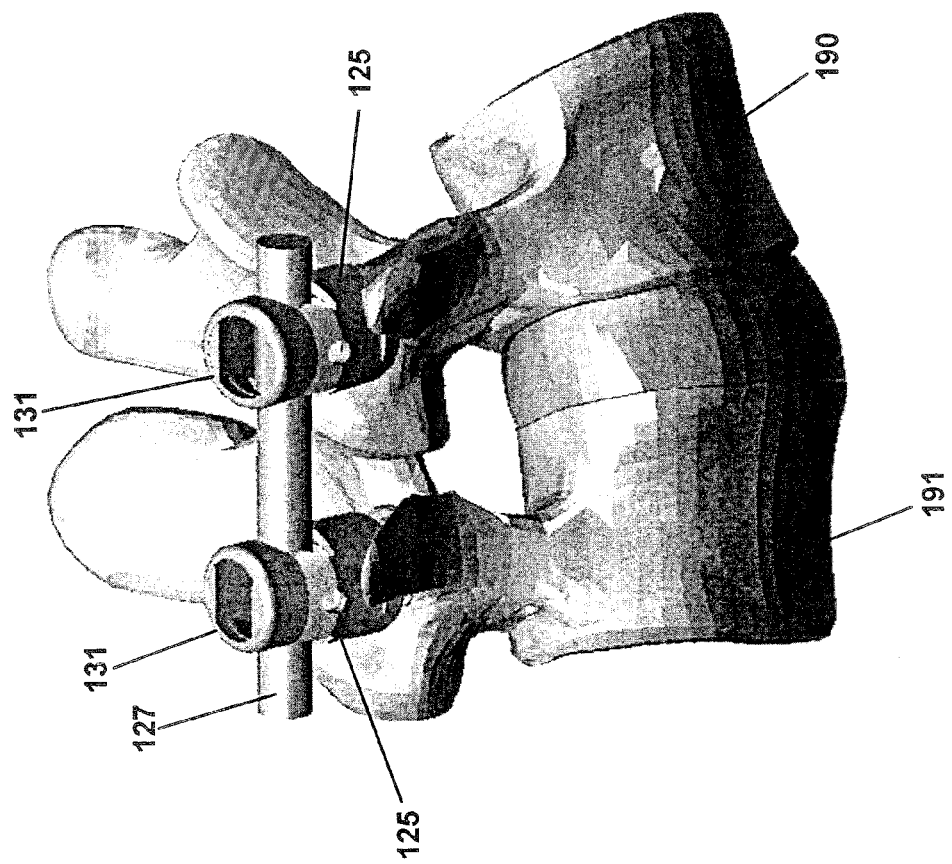
FIG. 3B is a lateral view of the rod/connector construct of FIG. 3A.

FIGS. 3A and 3B show rod/connector constructs being used in a single level spinal stabilization procedure. In conducting the procedure, connectors 125 are secured to vertebral bodies 190, 191 desired to be stabilized. Rods 127 are then pressed within the pockets 119 of the connectors 125 so as to be provisionally retained therein. In this manner, the connectors 125 function as temporary placeholders for the rods 127. The surgeon can then adjust the relative positioning of the vertebral bodies 190, 191 to achieve a desired relative positioning. For example, the vertebral bodies 190, 191 may be compressed together, distracted apart, or moved laterally relative to one another. During distraction or compression, the rods slide axially within the connectors 125. Once a desired spacial relationship between the vertebral bodies is achieved, the rods 127 are finally locked or clamped relative to the connectors 125 through the use of final fastening elements such as lock rings 131. Examples of other types of final fastening elements are described with respect to FIGS. 4-15. While FIGS. 3A and 3B show a single level procedure, connectors in accordance with the principles of the present disclosure can also be used in multi-level procedures using bent or straight rods.

As shown in FIGS. 4-15, a number of different fastening elements/devices can be used to fully or finally clamp the rod to the connectors after final adjustments have been made. For example, torque, no-torque or other final fastening techniques may be used. It will also be appreciated that the final fastening techniques that follow are fastening techniques that can be used with or without receivers having integral provisional retention capabilities.

Figure 4:
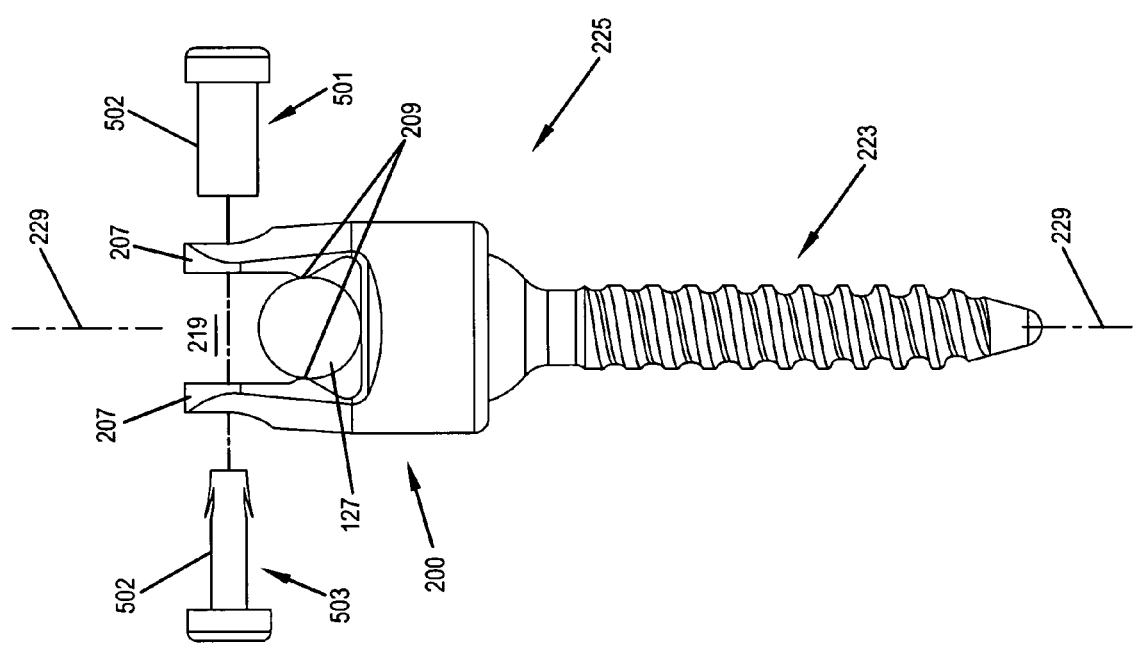
FIG. 4 is a side view of a second spinal fixation connector having features that are examples of inventive aspects in accordance with the principles of the present disclosure, a rod is shown provisionally retained in the connector.
Figure 6:
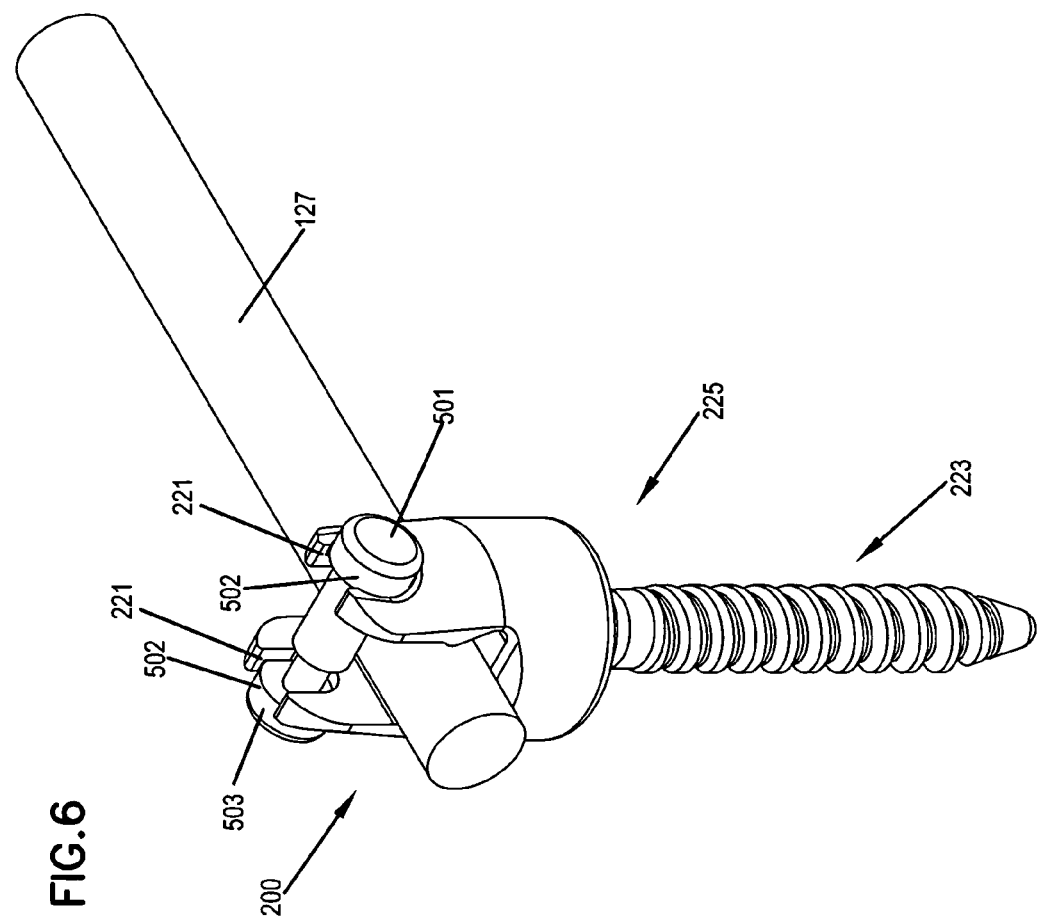
FIG. 6 is a perspective view of the spinal fixation connector of FIG. 5.
Figure 5:
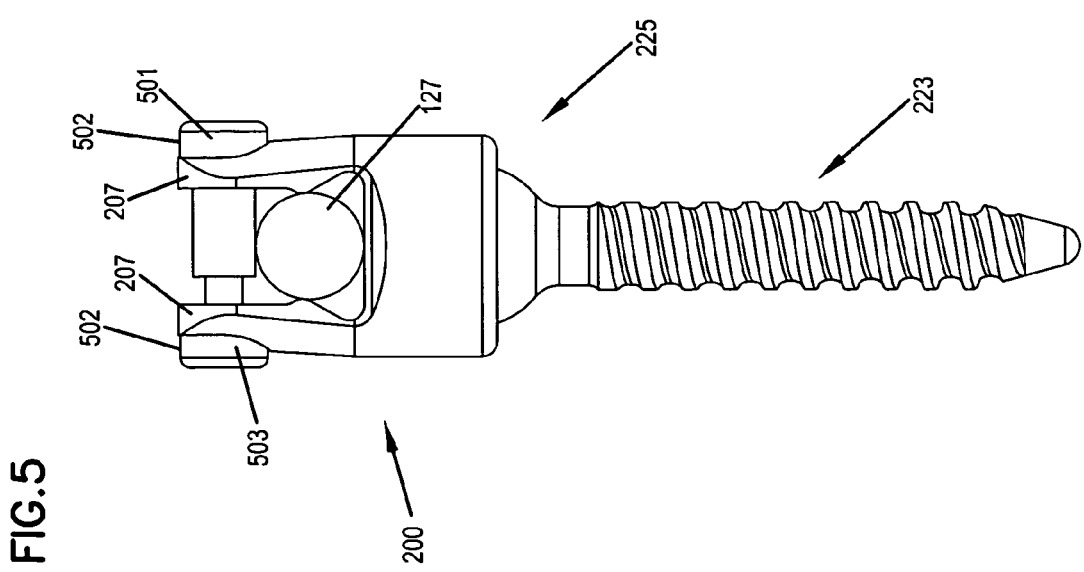
FIG. 5 is a side view of the spinal fixation connector of FIG. 4 in a final locked position.
Figure 8:
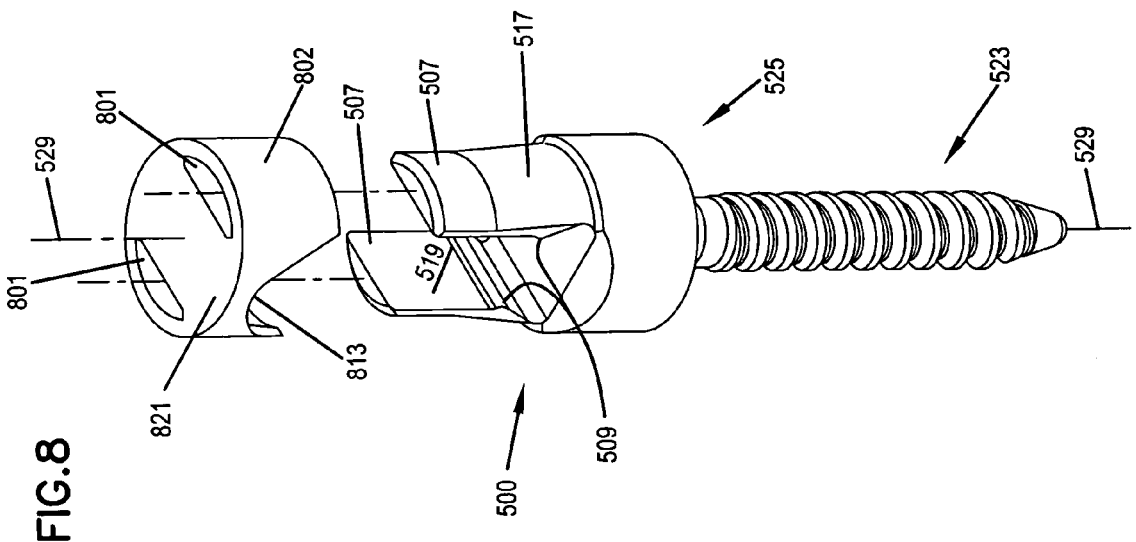
FIG. 8 is a perspective view of a fourth spinal fixation connector having features that are examples of inventive aspects in accordance with the principles of the present disclosure.

FIGS. 4-6 illustrate an embodiment of a spinal fixation connector 225 including a screw 223 coupled to a receiver 200. The receiver 200 defines a pocket 219. Similar to the embodiment of FIGS. 1 and 2, the connector 225 includes tabs 209 positioned within the pocket 219. The connector 225 further includes a lateral fastener in the form of a rivet arrangement 502 adapted to be coupled to the receiver 200. The receiver 200 includes slots 221 for receiving the rivet arrangement 502. The rivet arrangement 502 is adapted to be linearly inserted into the slots 221 of the receiver 200 in a direction perpendicular to a central axis 229 of the pocket 219. The rivet arrangement 502 includes intermating interlock parts (e.g., plug 503 and cap 501) that interlock to finally clamp a linking element, such as rod 127, within the pocket 219.

In general use, the rod 127 is first provisionally retained within the pocket 219 of the receiver (e.g., by tabs 209). While provisionally retained, the position of the rod can be adjusted relative to the connector 225. After the adjustment process is complete, the rod is finally locked in place by mounting the rivet arrangement 502 laterally across the pocket 219 of the receiver 200. As the rivet arrangement 502 is pressed together, the legs 207 of the receiver 200 are forced toward each other such that rod 127 is clamped between legs 207 and held in place. The rivet arrangement 502 preferably clamps the linking element with sufficient force to prevent the linking element 127 from sliding relative to the connector 225.

As indicated above, the lateral fastener of the fixation connector 225 is depicted as a rivet type arrangement including a plug 503 and a cap 501. The plug 503 is adapted to be linearly inserted into the cap 501 and interlock with the cap 501 after the plug 503 and cap 501 have been passed through the slots 221 of the receiver 200. FIGS. 5-6 show the connector 225 with the linking element 127 in a clamped position with the plug 503 and cap 501 in an interlocked position.

The plug 503 and the cap 501 of the rivet arrangement 502, as shown in FIGS. 4-6, may have a snap-fit connection to interlock. In one embodiment, the plug 503 can be the adapted to flex inwardly as the plug is inserted into the cap 501, and then self-expand to an interlocked position when fully inserted within the cap 501. Alternatively, the cap 501 can be adapted to expand to receive the plug 503, and then self-contract to an interlocked position when the plug 503 is fully inserted within the cap 501.

Figure 7:
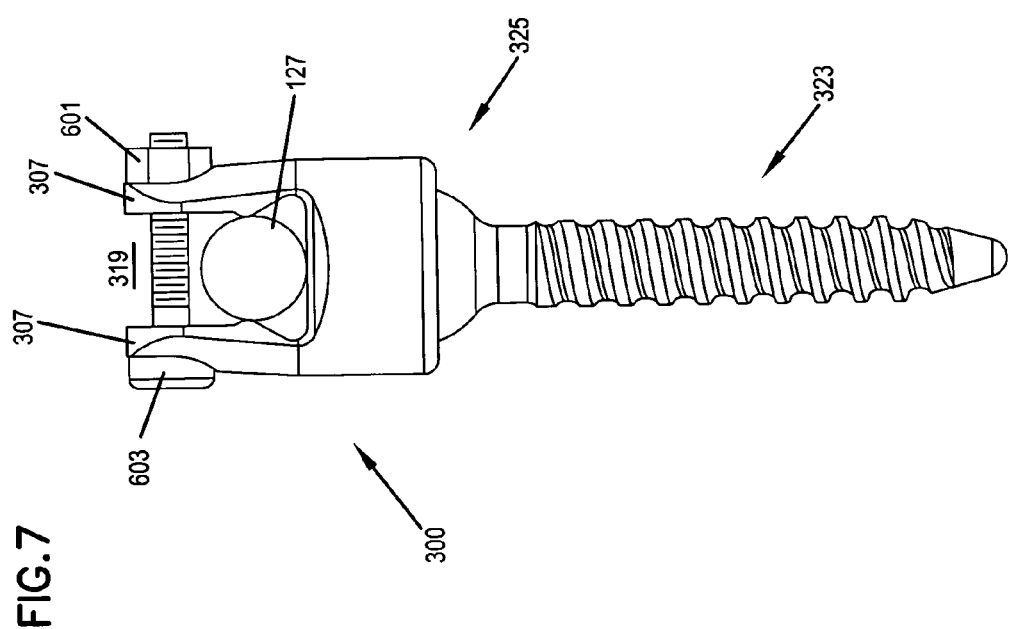
FIG. 7 is a side view of a third spinal fixation connector having features that are examples of inventive aspects in accordance with the principles of the present disclosure.

FIG. 7 illustrates a fixation connector 325 having another version of a lateral fastener for final fixation. The fixation connector 325 illustrated in the embodiment in FIG. 7 is essentially identical to the fixation connector 225 illustrated in FIGS. 4-6, except that in this embodiment, the final fastening technique used to clamp the linking element 127 to the connector 325 uses threaded components such as a bolt 601 and nut 603 arrangement. The connector 325 includes a screw 323 secured to a receiver 300. The receiver includes a pocket 319 defined between legs 307. By tightening the bolt and nut arrangement, the legs 307 of the receiver are drawn together to finally clamp a rod 127 held within the pocket 319. The nut 603 can be threaded on the bolt 601 with conventional tool for applying torque (e.g., wrench, pliers, etc.).

FIGS. 8-12 illustrate an example of another final fastening assembly used to clamp a rod 127 to a connector 525. The fixation connector 525 includes a screw 523 coupled to a receiver 500. The receiver 500 includes a pocket 519 defined between two legs 507. Provisional retaining tabs 509 project into the pocket 519. The connector 525 also includes a sleeve type fastener 802 adapted to be linearly slid over the legs of the receiver 500. In one embodiment, the sleeve 802 is secured to the receiver 500 with a friction fit. The sleeve 802 is adapted to lock the rod 127 within the pocket 519 of the receiver 500.

In general use, the rod 127 is first provisionally retained within the pocket 519 (e.g., by tabs 509). After any necessary adjustments have been made, the rod 127 is finally locked within the pocket of the receiver 500 by linearly sliding the sleeve 802 downwardly over the legs 507 of the receiver 500. The sleeve 802 and/or the legs 507 preferably include contact surfaces with a taper that causes the legs 507 of the receiver 500 to flex inwardly to compress the rod 127 as the sleeve 802 is slid downwardly over the legs 507. In this manner, that the rod 127 is clamped within the receiver 500. In certain embodiments, a Morse taper can be used.

As shown in FIGS. 8-11, the legs 507 of the receiver 500 include outer contact surfaces 517 that taper outwardly at an angle relative to a central axis 529 of the receiver 500 as the surfaces 517 extend in a downward direction.

Figure 10:
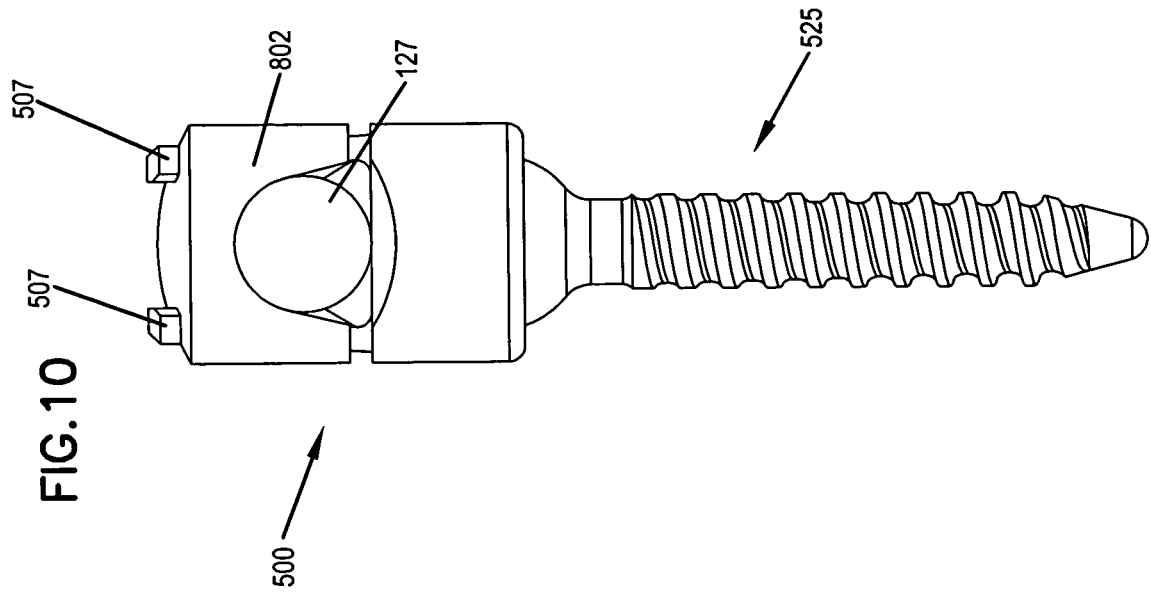
FIG. 10 is a side view of the spinal fixation connector of FIG. 9.
Figure 9:
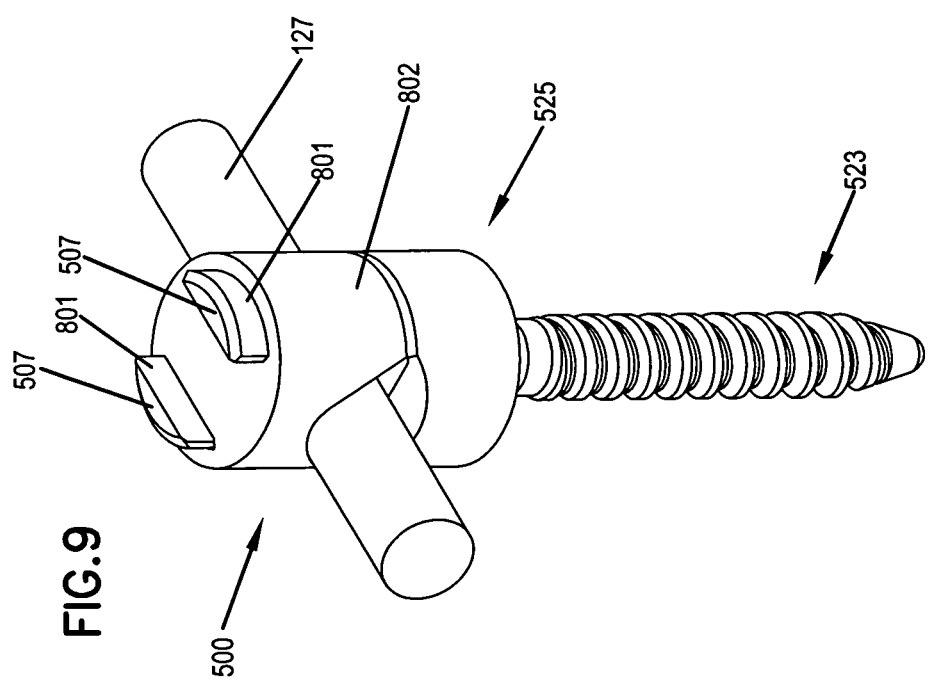
FIG. 9 is a perspective view the spinal fixation connector of FIG. 8 in a locked position.

The sleeve 802 shown at FIGS. 8-12 includes a top wall 821 defining through-holes 801 adapted to slidably receive the legs 507 of the receiver 500. The legs 507 of the receiver 500 preferably have transverse cross-sections that generally match the shape of the perimeter of the holes 801. In some embodiments, the sleeve 802 also includes a contoured underside 813 that defines a concavity or pocket adapted to engage the top side of the rod 127 when the sleeve is mounted on the receiver 500. FIGS. 9-10 show the connector 525 with the linking element 127 in a clamped position with the sleeve 802 coupled to the receiver 500.

Figure 12B:
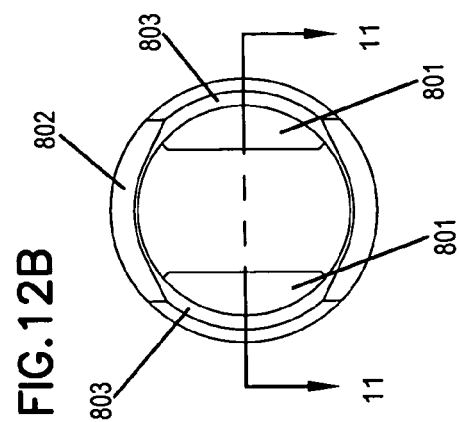
FIG. 12B is a bottom view of the locking sleeve of FIG. 12A.
Figure 12A:
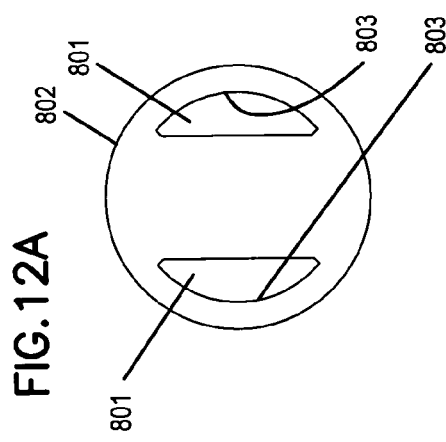
FIG. 12A is a top view of a locking sleeve of the connector shown in FIGS. 8-11.
Figure 11:
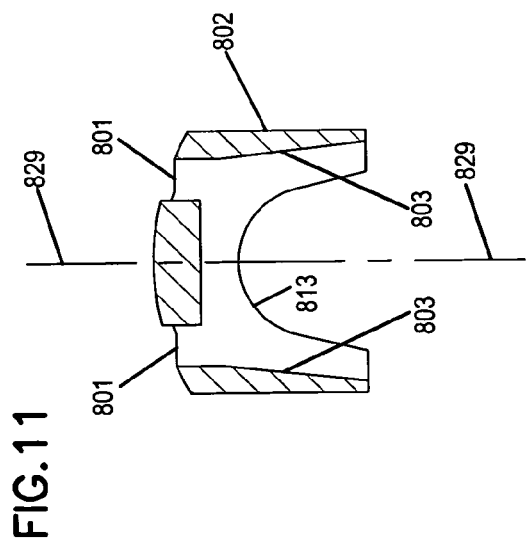
FIG. 11 is a cross-sectional view taken along section line 11-11 of FIG. 12B.

Referring to FIG. 11, the sleeve 802 is depicted including opposing inner contact surfaces 803 adapted to engage the outer contact surfaces 517 of the legs 507 when the sleeve 802 is mounted on the receiver 500. The contact surfaces 803 taper outwardly at an angle relative to a central axis 829 of the sleeve 802 as the contact surfaces 803 extend in a downward direction. In one embodiment, the taper angle of the inner contact surfaces 803 of the sleeve 802 generally matches the taper angle of the outer contact surfaces 517 of the legs 507. The relative tapers of the contact surfaces 517, 803 cause the legs 507 to flex inwardly when the sleeve 802 is slid downwardly over the legs 507. Thus, a rod 127 can be finally clamped in the pocket 519 by sliding the sleeve 802 over the legs 507 of the receiver 500. FIG. 12A illustrates a top view of the sleeve 802 and FIG. 12B illustrates a bottom view of the sleeve 802 wherein the taper of the opposing inner vertical walls 803 is illustrated.

Figure 13:
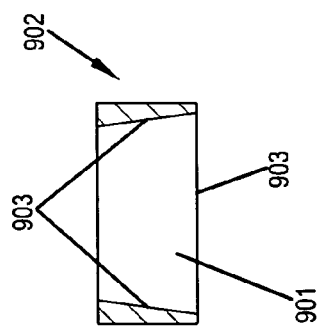
FIG. 13 is a cross-sectional view of an alternative locking sleeve.

In FIG. 13, an alternative sleeve 902 adapted for use with the receiver 500 is illustrated. The sleeve 902 has a complete ring type structure, with a single through-hole 901 defined by an interior surface 903. The ring 902 is shaped and sized to be linearly slid over the legs 507 of the receiver 500 to cause the legs 507 to flex inwardly to finally lock a rod 127 within the receiver 500. Similar to the contact surfaces 803 of the sleeve, 802, the surface 903 may be tapered to generally match or otherwise cooperate with the taper of the contact surfaces 517 of the receiver 500 so as to cause final clamping of the rod within the receiver 500.

Figure 15:
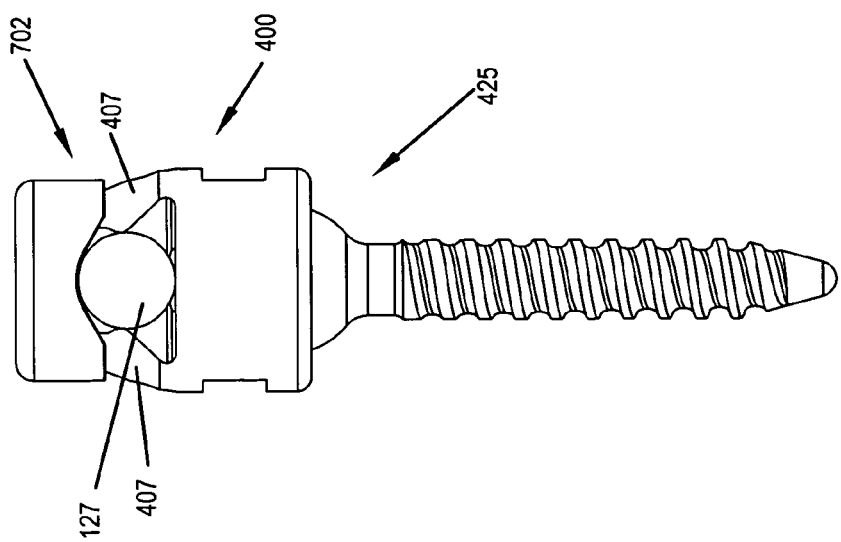
FIG. 15 is a side view of the spinal fixation connector of FIG. 14 in a locked position.
Figure 14:
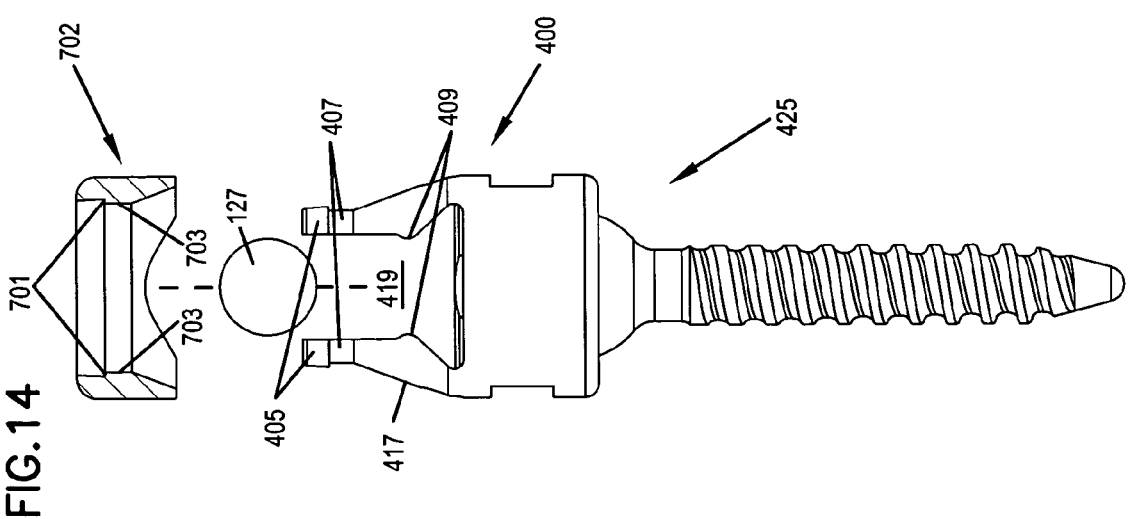
FIG. 14 is a side view of a fifth spinal fixation connector having features that are examples of inventive aspects in accordance with the principles of the present disclosure, the connector is shown in partial cross-section and oriented in a non-locked position.

FIGS. 14 and 15 illustrate another embodiment of a fixation connector 425 including a tapered clamping arrangement. The fixation connector 425 includes a receiver 400 including legs 407 between which a pocket 419 is defined. Provisional retaining tabs 409 project into the pocket 419. A sleeve 702 is used to finally lock a rod within the receiver 400. The sleeve 702 includes tapered interior contact surfaces 703 that cooperate with tapered exterior contact surfaces 417 of the receiver 400 to cause the rod to be clamped and locked within the receiver 400 when the sleeve 702 is slid over the legs 407 of the receiver 400.

The fixation connector illustrated in the embodiment in FIGS. 14 and 15 operates similar to the fixation connector illustrated in FIGS. 8-12, except that in this embodiment, the legs 407 of the saddle 400 include discrete locking structures 405 (e.g., tabs, ramps, teeth, and etc.) on the outer vertical surfaces 417 to assist in retaining the sleeve 702 on the receiver 400. The sleeve 702 may include locking structures 701 (e.g., tabs, ramps, ratchet, and etc.) adapted to engage with the locking structures 405 of the receiver 400 to retain the sleeve 702 in an interlocked position after it has been inserted over the legs 407 of the receiver 400. Sleeves 902 of the type shown in FIG. 13 could also be used in combination with the saddle 400.

Figure 16:
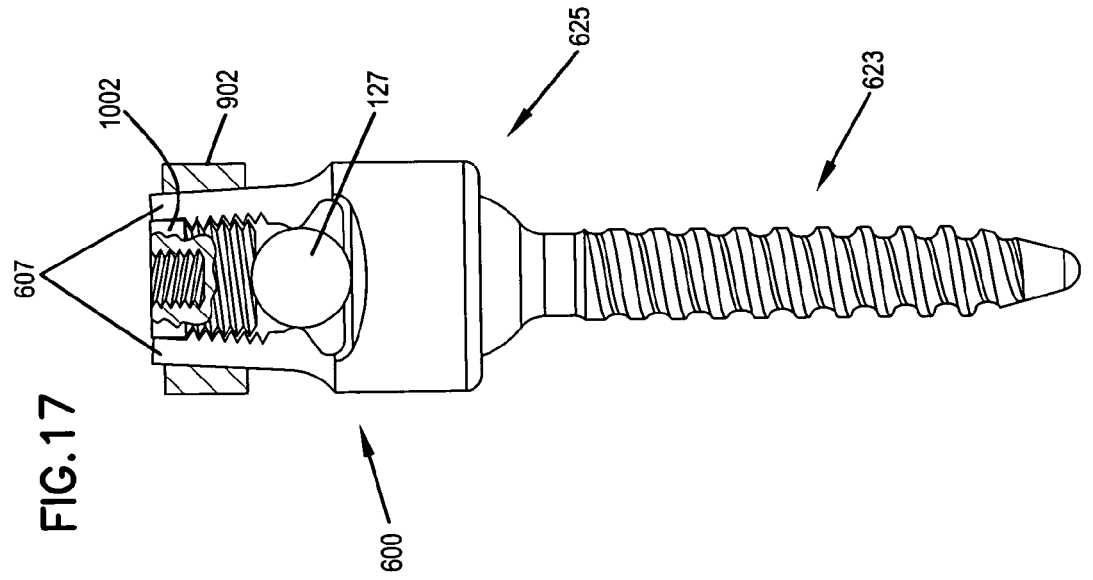
FIG. 16 is a side view of a sixth spinal fixation connector having features that are examples of inventive aspects in accordance with the principles of the present disclosure, the connector is shown provisionally retaining a rod.
Figure 17:
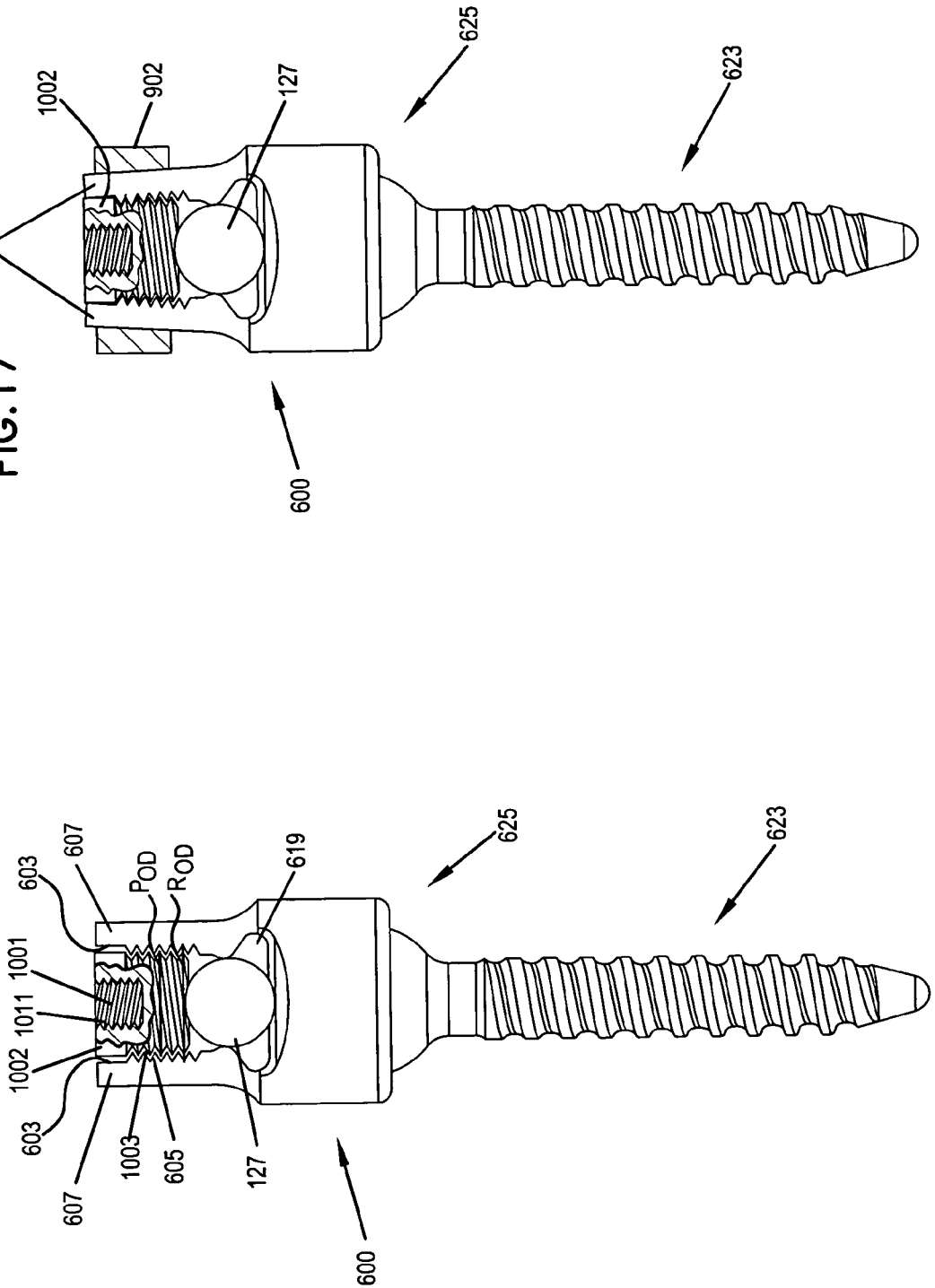
FIG. 17 is a side view of the spinal fixation connector of FIG. 16 in a locked position.
Figure 18:
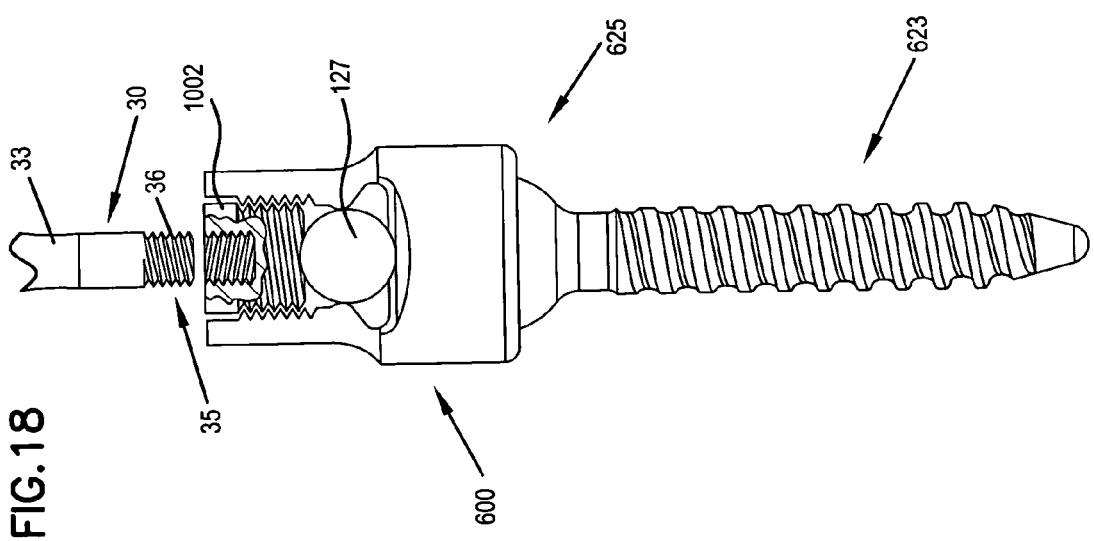
FIG. 18 is side view of the spinal fixation connector of FIG. 16 used in combination with a detachable tool.

FIGS. 16-18 illustrate another embodiment of a spinal fixation connector 625 that includes provisional tightening means used in the stabilization of the vertebrae. The fixation connector 625 includes a bone screw 623 or other anchor. The connector also includes a receiver 600 coupled to the bone screw 623. The receiver 600 includes legs 607 that define an interior pocket 619 for receiving a linking element such as rod 127. The connector 625 further includes a provisional tightening component in the form of a plug 1002 adapted to provisionally secure the rod 127 within the interior pocket 619 of the receiver 600. A sleeve 902 is used to finally lock the rod 127 within the receiver 600.

In use, the rod 127 is first placed in the pocket 619 of the receiver 600. After the rod 127 has been placed into the pocket 619, the rod 127 is provisionally retained in the pocket by threading the plug 1002 into the pocket 619. Thereafter, final locking of the rod 127 within the receiver 600 is accomplished by sliding the sleeve 902 over the legs 607 of the receiver 600. As the sleeve 902 is slid downwardly, the legs 607 flex inwardly to clamp the rod in the final position.

In FIGS. 16-18, the legs 607 of the receiver 600 include opposing interior surfaces 603 defining internal threads 605. The threads 605 define an inner thread diameter (measured between thread peaks) and an outer thread diameter (measured between thread valleys). The outer thread diameter $R_{OD}$ of the receiver 600 is labeled at FIG. 16.

As shown in FIGS. 16-18, the plug 1002 preferably includes a generally cylindrical body with external threads 1003. The plug 1002 is adapted to be loosely threaded in between the legs 607 of the receiver wherein the external threads 1003 of the plug 1002 engage the internal threads 605 of the receiver 600. The external threads 1003 of the plug 1002 define an inner thread diameter (measured between thread valleys) and an outer thread diameter (measured between thread peaks). The outer thread diameter $P_{OD}$ of the plug 1002 is labeled at FIG. 16.

The outer diameter $P_{OD}$ of the plug 1002 is sized smaller than the outer diameter $R_{OD}$ of the receiver 600 so that the plug 1002 can be loosely threaded between the legs 607 of the receiver 600. For certain applications, the plug 1002 can be advanced until it makes contact with the rod 127 such that the rod is provisionally clamped within the pocket 619. In other applications, the plug 1002 is threaded into the pocket 619 to a depth short of engaging the rod 127. In such an application, the plug 1002 provisionally retains the rod in the pocket (e.g., keeps the rod from being lifted from the pocket) without applying a clamping force to the rod.

The plug 1002 also may include structure 1001 adapted to accept a tool 30. The tool accepting structure of the plug 1002 is depicted as a slot 1001 including internal threads 1011 in FIGS. 16-18. The tool 30 as seen in FIG. 18 includes a shaft 33 having a tip 35 with external threads 36 adapted to engage the threads 1011 of the slot 1001 of the plug 1002. The tool 30 is adapted to be used to drive the plug 1002 in between the legs 607 of the receiver 600. Although shown as having intermating threads in FIG. 18, this embodiment of the tool and the plug is only a representative example, and other means of engagement allowing for rotational driving of the plug 1002 are within the spirit of the invention. For example, in alternative embodiments, the plug could include a socket such as a hexagonal socket for receiving a hex-driver or other tool.

Once provisionally tightened by the plug 1002, the rod 127 can be finally, non-provisionally fastened with any fastening technique discussed above that is adapted to cause inward flexing in of the legs 607 of the receiver 600 to clamp the linking element 127 within the pocket 619. In FIG. 17, the sleeve 902 is used to provide final locking of the rod 127 within the connector 625.

In use, the rod 127 is provisionally secured with the receiver 600 by threading the plug 1002 into the pocket 619 such that the rod 127 is captured in the pocket 619. After any necessary positional adjustments have been made, rod 127 is locked in place by sliding the sleeve 902 over the exterior of the receiver 600. As the sleeve 902 is slid over the receiver 600, the legs 607 deflect inwardly to lock the rod 127 in a final position. As the legs 607 are deflected inwardly, the difference between the plug outer thread diameter $P_{OD}$ and receiver outer thread diameter $R_{OD}$ decreases until the rod 127 is clamped within the receiver 600. The sleeve 902 and/or the legs 607 may include contact surfaces with a taper as discussed above to cause the legs 607 of the receiver 600 to flex inwardly to lock the rod 127 in it final position.

In certain embodiments, the plug 1002 can be threaded out of the receiver after final clamping. In other embodiments, the plug 1002 can be left within the receiver after final tightening.

Figure 19:
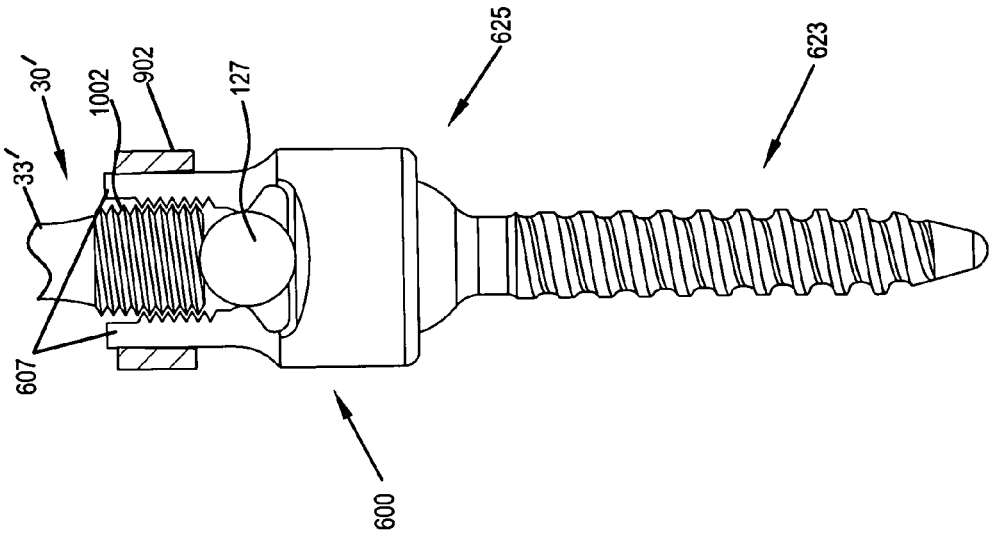
FIG. 19 is a side view of a seventh a spinal fixation connector having features that are examples of inventive aspects in accordance with the principles of the present disclosure.

As described above, a tool 30 adapted to engage the slot 1001 of the plug 1002 can be used to thread in and/or out the plug 1002. The tool 30 can also be used to apply a linear force (e.g., in an upward direction) that opposes the force required to push the sleeve 902 linearly over the receiver 600. In this manner, the surgeon is able to slide the sleeve 902 around the legs 607 of the connector without having a substantial amount of linear force transferred to the patient. Once the rod 127 is locked in a final position, the tool tip 35 of the tool 30 can be threaded out of the slot 1001 of the plug 1002 leaving the plug 1002 within the receiver, or can be used to thread out the plug 1002. FIG. 19 shows an alternative tool 30' having a shaft 33' that is integral with the plug 1002.

Figure 20:
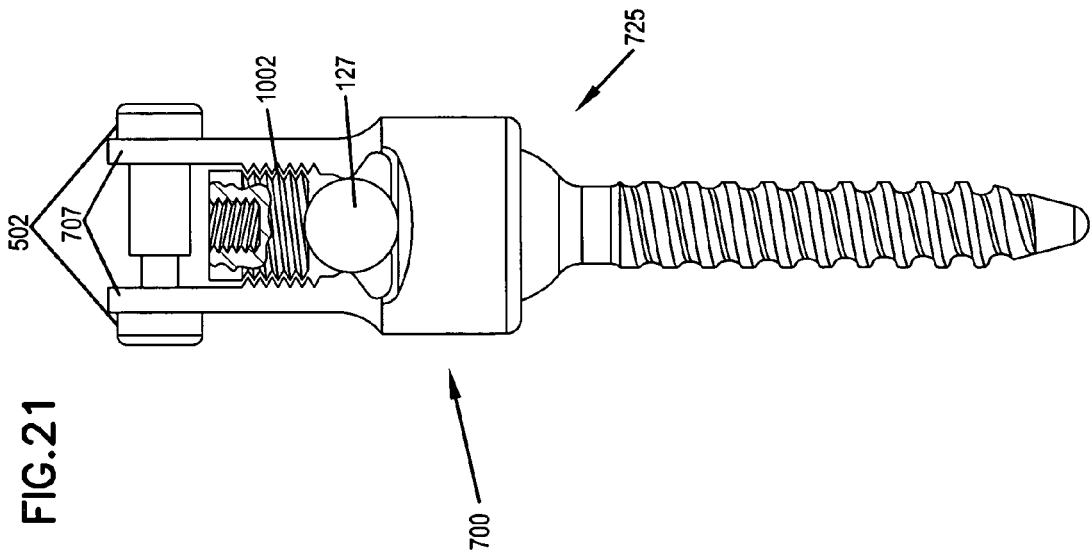
FIG. 20 is a side and partial cross-sectional view of an eighth spinal fixation connector having features that are examples of inventive aspects in accordance with the principles of the present disclosure.

FIG. 20 shows an alternative final fasting arrangement for locking the rod 127 in a final position relative to the receiver 600. The final fastening arrangement includes an outer sleeve 1102 that cooperates with an inner sleeve 902' to lock the rod in its final position. The inner sleeve 902' can be a solid/continuous ring or a slotted ring.

The inner sleeve 902' includes generally a cylindrical body including an outer sidewall 904 extending between a top end 905 and a bottom end 906 of the sleeve 902'. The outer sidewall 904 of the sleeve 902' tapers out at an angle relative to the central axis of the sleeve 902' such that the sleeve 902' defines a minor outer diameter at its top end 905 and a major outer diameter at its bottom end 906. The sleeve 902' may or may not have an internal taper.

The outer sleeve 1102 includes an interior surface 1104 defining an opening that extends between a top end 1105 and a bottom end 1106 of the sleeve 1102. The interior surface 1104 of the outer ring 1102 defines a taper angle that matches the taper angle of the outer surface 904 of the first ring 902'. The outer sleeve 1102 defines a major inner diameter at the bottom end 1106 and a minor inner diameter at the top end 1105. The opening defined by the sleeve 1102 is sized to receive the inner sleeve 902'.

In use, the inner sleeve 902' is slid over the receiver 600 to lock the rod in a final position relative to the receiver 600. After sliding the inner sleeve 902' into position, the outer sleeve 1102 is swaged over the inner sleeve 902' to compress the inner sleeve 902'.

Figure 21:
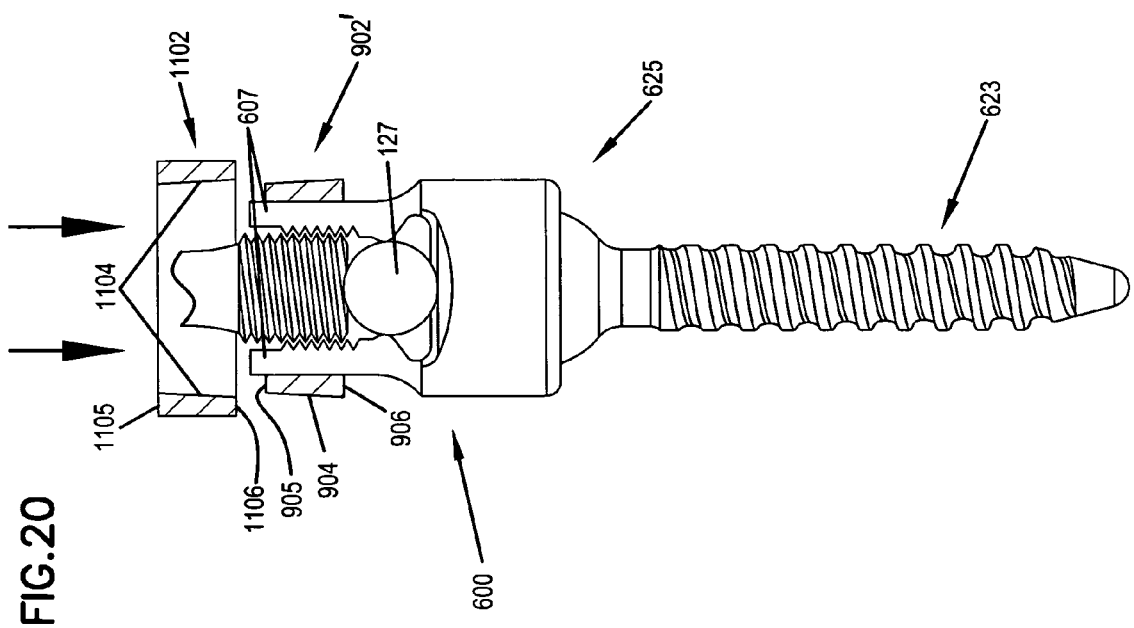
FIG. 21 is a side view of a ninth spinal fixation connector having features that are examples of inventive aspects in accordance with the principles of the present disclosure.

FIG. 21 shows a fixation connector 725 including a receiver 700 and a plug 1002 for provisionally retaining a rod 127 in the receiver 700. The connector 725 also includes a final fastener 502 of the type described with respect to the embodiment of FIG. 4.

In use, the plug 1002 is loosely threaded in the receiver 700 to provisionally secured the rod 127 therein. After the rod has been adjusted to its final position, the fastener 502 is installed. During installation of the fastener 502, lateral loading is applied to the legs 707 of the receiver causing the legs to flex together and clamp the rod 127. As the legs 707 flex together, a radial spacing between the legs 707 of the receiver and the plug 1002 is reduced in size. Other types of final fasteners such as the nut/bolt type arrangement described previously above can also be used in combination with a plug type provisional tightening component.

Figure 22:
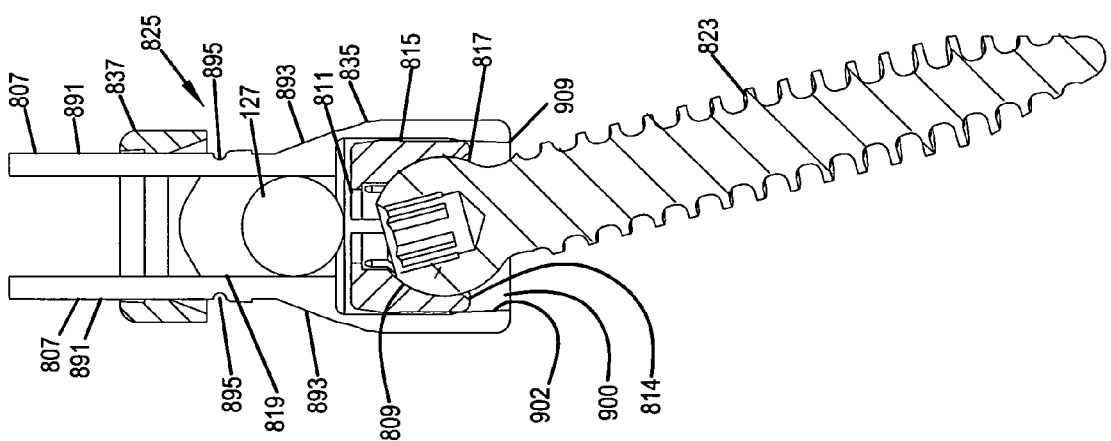
FIG. 22 is a cross-sectional view of a tenth spinal fixation connector having features that are examples of inventive aspects in accordance with the principles of the present disclosure, the connector is shown with a rod provisionally retained therein.
Figure 23:
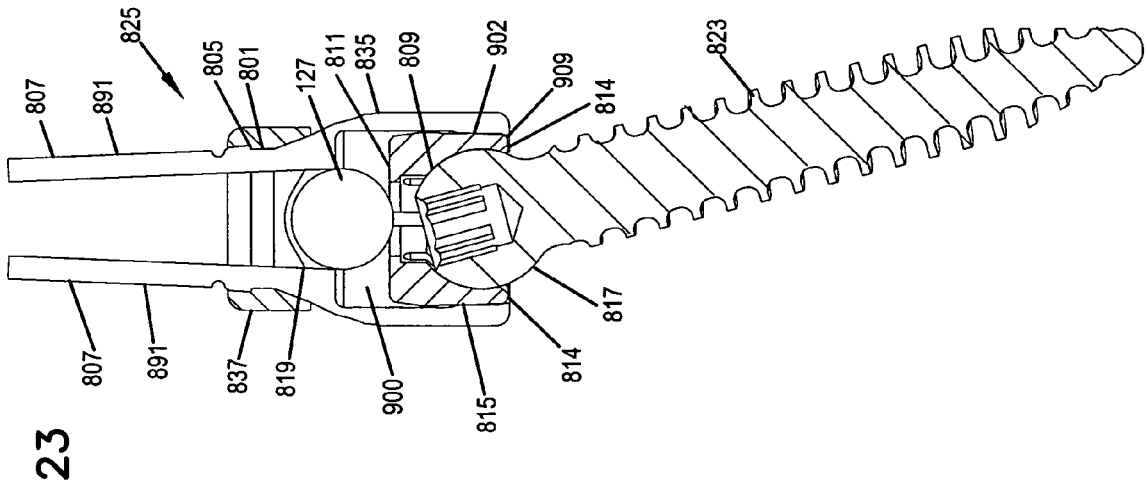
FIG. 23 is a cross-sectional view of the spinal fixation connector the FIG. 22 showing the connector in a fully fastened position.

FIGS. 22 and 23 illustrate another embodiment of a fixation connector 825 for use in stabilization of the vertebrae. The embodiment shown in FIGS. 22 and 23 has a polyaxial screw locking arrangement having features similar to embodiments disclosed in U.S. Pat. Nos. 5,863,293, 5,964,760, and 6,132,432, which are incorporated by reference in their entireties. It will be appreciated that the polyaxial screw locking arrangement depicted in FIGS. 22 and 23 can also be used in the previously described embodiments of FIGS. 1-21.

In the embodiment shown in FIGS. 22 and 23, the fixation connector 825 includes a receiver 835 having rod-receiving pocket 819 and an anchor-receiving pocket 900. The rod-receiving pocket 819 is defined between legs 807 of the receiver 835. The anchor-receiving pocket 900 is adapted to house a retainer 815. A screw 823 is coupled to the retainer 815 within the pocket 900. The retainer 815 preferably includes a generally spherical cavity 809 that receives a generally spherical head 817 of the screw 823. The relative shapes of the head 817 and cavity 809 allow the head 817 to pivot/rotate within the retainer 815 to allow the orientation of the axis of the screw 823 to be angularly adjusted relative to the receiver 835 prior to final fixation. The connector 825 also includes a final fastener such as a sleeve 837 for locking the screw 823 at a final axial position relative to the receiver 835, and for locking a rod 127 within the rod-receiving pocket 819.

The retainer 815 includes flexible legs 814 that define the cavity 809. When the retainer 815 is mounted in the anchor-receiving pocket 900, a top end 811 of the retainer 815 is exposed to the rod-receiving pocket 819 of the receiver 835.

The anchor-receiving pocket 900 of the receiver 835 includes a tapered internal surface 902 defining a diameter that reduces in size as the surface 902 extends downwardly away from the rod-receiving pocket 819. The anchor-receiving pocket 900 includes a lower opening 909 through which the retainer 815 and the screw 823 can be bottom loaded into the receiver 835.

To bottom load the screw 823 into the receiver 835, the retainer 815 is first inserted into the anchor-receiving pocket 900 through the lower opening 909. After the retainer has been inserted into the anchor-receiving pocket 900, the head 817 of the screw 813 is inserted through the lower opening 909 and snapped into the cavity 809 of the retainer 815. When the head 817 of the screw 823 is inserted into the cavity 809, the retainer 815 expands (e.g., the legs flex outwardly) thereby preventing the retainer 815 and the screw head 817 from being removed from the pocket 900 without using a removal tool.

In use, the assembled connectors 825 are anchored to bones desired to be stabilized. A rod is then inserted into the rod-receiving pockets 819 of the connectors 825 to interconnect the anchored connectors and thereby form a rod/connector construct. The rod 127 is provisionally retained within the pockets 819 by linearly sliding the sleeve 837 downwardly over upper portions 891 of the legs of the receivers 835, as shown in FIG. 22. In certain embodiments, the upper portions 891 of the legs are not tapered, or include only a slight taper and are configured to loosely engage the sleeve 837 or to engage the sleeve 837 with a slight friction fit without causing the rod and screw to be finally locked in position.

While the rod is provisionally retained, adjustments can be made to the rod/connector construct. For example, the connectors 825 can be moved relative to the rod 127 and the rod 127 can be rotated within the connectors 825. Also, the axial position of the screws relative to their corresponding receivers can be adjusted. After final adjustments have been made to the rod/connector construct, the locking sleeves 837 are slid downwardly to a final locking position as shown in FIG. 23. As the sleeves 837 are moved to the final locking position, the sleeves 837 force the rod 127 downwardly within the pockets 819. As the rod 127 is forced downwardly, the rod 127 engages the retainers 815 within the anchor-receiving pockets 900 causing the retainers 815 to be compressed by the tapered surfaces 902 of the pockets 900. When compressed, the retainers 815 clamp their corresponding screw heads 817 to lock the screws 823 at the final desired angle relative to their corresponding receivers 835. Also, when the sleeves 837 are in the position of FIG. 23, the legs 807 of the receivers 835 are clamped against the rod 127 to finally lock the rod 127 in position relative to the connectors 825.

In certain embodiments, the clamping action can be provided by tapered regions 893 that have an increased taper angle as compared to the upper portions 891. The sleeves 837 can include locking structures 801 that interlock with locking structures 805 of the receiver 835 (e.g., in a snap-fit relationship) to retain the sleeve 837 in the locked position. The legs 807 can include notches 895 for facilitating breaking the upper portions 891 away from the receiver 835 to reduce the profile of the connector 825 after the rod has been locked in position.

Figure 24:
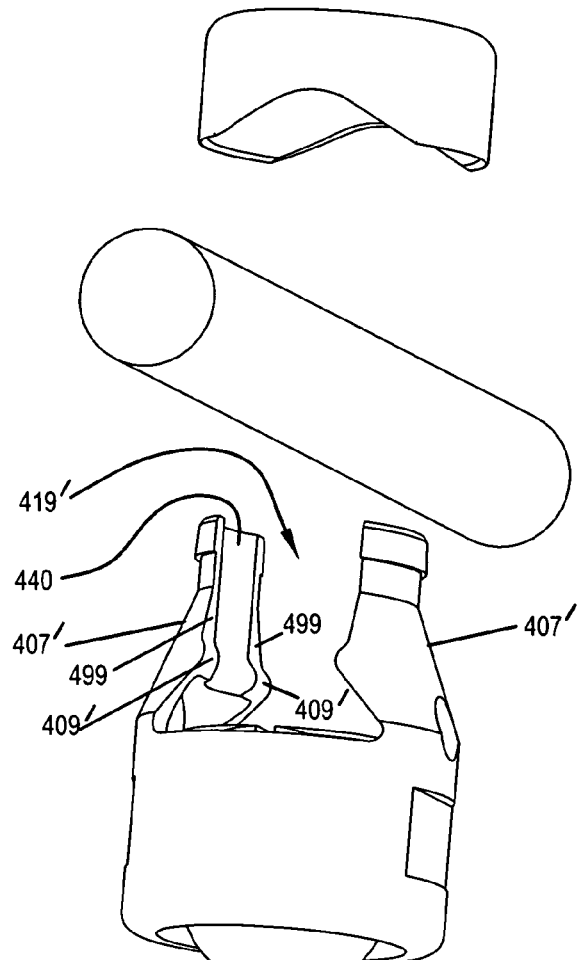
FIG. 24 is a perspective view of an eleventh spinal fixation connector having features that are examples of inventive aspects in accordance with the principles of the present disclosure.
Figure 25:
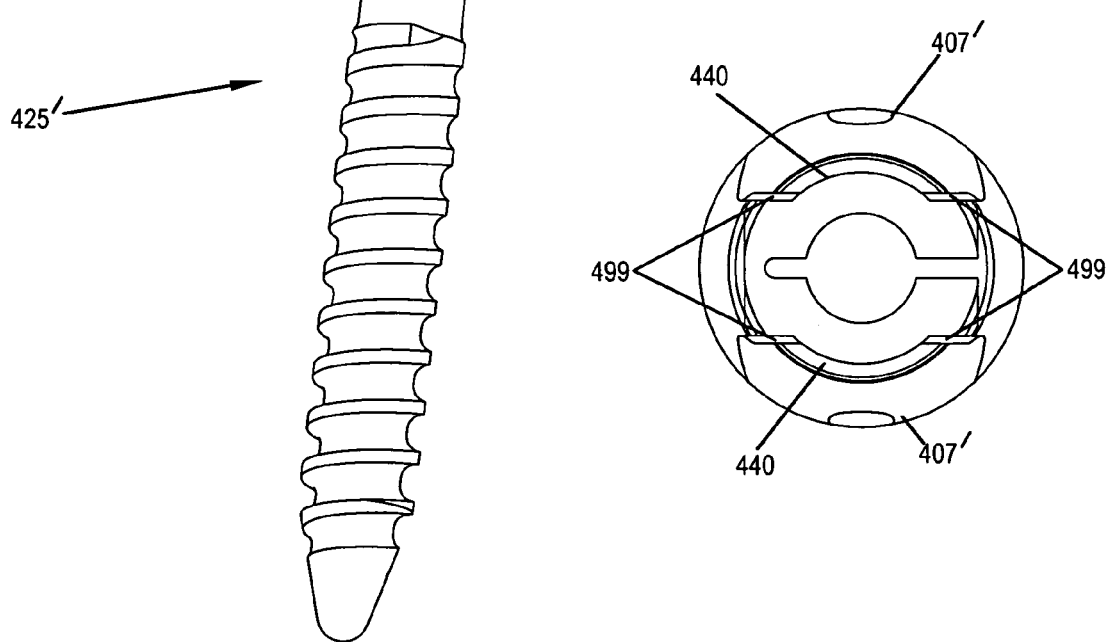
FIG. 25 is a top view of the spinal fixation connector of FIG. 24.

FIGS. 24 and 25 illustrate another embodiment of a fixation connector 425' and the same general components as the fixation connector 425 of FIGS. 14 and 15. The fixation connector 425' has been modified to include a pocket 419' that is adapted to receive curved rods. Specifically, the pocket 419' is defined between legs 407' having inner opposing surfaces that define opposing recessed regions 440. The recessed regions 440 (e.g., hollowed out regions) extend from the top ends of the legs downwardly through provisional retaining tabs 409'. The recessed regions 440 are defined between upright ridges 499 that extend from the top ends of the legs downwardly through the tabs 409'. When a rod is clamped within the pocket 419', the ridges 499 contact the rod while the recessed regions 440 provide space for the accommodating rod curvature.

The embodiments disclosed herein are all depicted including anchors in the form of screws. It will be appreciated that other anchors such as pins, hooks, rivets or other structures could also be used.

The embodiments disclosed herein include various components such as receivers, anchors, sleeves, rods, fasteners and other components. It will be appreciated that these components can be manufactured from different types of material. Example materials include Titanium, Nitinol, Stainless Steel, Thermoplastic polymers, Thermoset polymers as well as other materials.

From the foregoing detailed description, it will be evident that modifications and variations can be made in the devices of the invention without departing from the spirit or scope of the invention. Therefore, it is intended that all modifications and variations not departing from the spirit of the invention come within the scope of the claims and their equivalents.

We claim:

1. A fixation connector for securing a linking element to a bone, the fixation connector comprising:
 a bone anchor;
 a receiver coupled to the bone anchor, the receiver including:
  a seat portion including a planar surface opposite an open top end of the receiver;
  legs extending upward from the seat portion to the open top end, the legs defining a pocket for receiving the linking element; each leg having a tapered exterior surface and a locking geometry, and
  a first tab that projects into the pocket for provisionally retaining the linking element within the pocket, wherein with the linking element resting against the planar surface of the seat portion, the first tab exerts a provisional clamping force on the linking element to restrict axial and/or rotational movement of the linking element relative to the receiver; and
 a fastening member slidably couplable to the receiver including a locking geometry configured to engage the locking geometry of the legs; and a tapered surface on the fastening member, the tapered surface operative to move the legs toward one another and thereby exert a final clamping force on the linking element to clamp the linking element received in the pocket of the receiver when the fastening member is slidably coupled to the receiver;
 wherein the final clamping force is greater than the provisional clamping force.

2. The fixation connector of claim 1, wherein the first tab is integral with one of the legs.

3. The fixation connector of claim 1, wherein the first tab includes an upper ramp surface.

4. The fixation connector of claim 1, wherein the legs include first and second legs, and wherein the first tab is integral with the first leg and a second tab is integral with the second leg.

5. The fixation connector of claim 1, wherein the fastening member includes a sleeve that is mounted about an exterior of the legs.

6. The fixation connector of claim 1, wherein the anchor is a bone screw.

7. The fixation connector of claim 6, wherein the bone screw comprises a polyaxial screw.

8. The fixation connector of claim 1, wherein the fastening member is a sleeve.

9. A fixation connector for securing a linking element to a bone, the fixation connector comprising:
 a bone anchor;
 a receiver coupled to the bone anchor, the receiver including:
  a seat portion including a planar surface opposite an open top end of the receiver;
  legs extending upward from the seat portion to the open top end, the legs defining a pocket for receiving the linking element;
  wherein the legs each have a discrete locking structure; and
 a first tab that projects into the pocket for provisionally retaining the linking element within the pocket, wherein with the linking element resting against the planar surface of the seat portion, the first tab exerts a provisional clamping force on the linking element to restrict axial and/or rotational movement of the linking element relative to the receiver; and a final fastening structure for retaining the linking element in a final position within the pocket, the final fastening structure including a sleeve mounted about an exterior of the legs;

wherein the sleeve includes an interior taper for compressing the legs together as the sleeve is mounted about a tapered exterior of the legs to exert a final clamping force on the linking element, the final clamping force being greater than the provisional clamping force;

wherein the sleeve further includes a structure configured to mate with the discrete locking structure of each of the legs.

10. A fixation connector for securing a linking element to a bone, the linking element having a cross-sectional shape defining a maximum width of the linking element, the fixation connector comprising:

a bone anchor; and a receiver coupled to the bone anchor, the receiver including:

a seat portion including a planar surface opposite an open top end of the receiver;

legs extending upward from the seat portion to the open top end, the legs defining a pocket for receiving the linking element, wherein the legs each have an interior surface and an exterior surface, wherein the exterior surface tapers at an angle; and means for automatically provisionally retaining the linking element within the pocket when the linking element is inserted in the pocket and resting against the planar surface of the seat portion;

wherein the means for provisionally retaining the linking element within the pocket exerts a provisional clamping force on the linking element at a position just above the maximum width of the linking element when the linking element is resting against the seat portion to restrict axial and/or rotational movement of the linking element relative to the receiver.

11. The fixation connector of claim 10, further comprising:

a locking structure including an interior surface that tapers at an angle, wherein when the linking element is within the pocket of the receiver, the angle at which the interior surface of the locking structure tapers complements the angle at which the exterior surface of the first leg tapers and the angle at which the exterior surface of the second leg tapers.

12. A fixation connector for securing a linking element to a bone, the fixation connector comprising:

a linking element;

a bone anchor;

a receiver coupled to the bone anchor, the receiver including a seat portion including a planar surface opposite an open end of the receiver and legs extending upward from the seat portion toward the open end defining a pocket for receiving the linking element;

the receiver including means for automatically exerting a provisional clamping force on the linking element to restrict axial and/or rotational movement of the linking element relative to the receiver when the linking element is inserted in the pocket and resting against the planar surface of the seat portion;

a sleeve configured to be snappingly coupled to the receiver; having a bottom surface and means for moving the legs toward one another such that the legs clamp the linking element received in the pocket of the receiver;

wherein when the sleeve is snappingly coupled to the receiver, the bottom surface of the sleeve abuts the linking element received in the pocket of the receiver.

13. A fixation system for securing a linking element to a bone, the fixation system comprising:

a linking element;

a bone anchor;

a receiver coupled to the bone anchor, the receiver including:

a seat portion including a planar surface opposite an open top end of the receiver;

an upper portion including a first leg and a second leg defining a pocket for receiving the linking element, wherein the first leg and second leg each have an upper end having a discrete locking structure; and a first projection that extends into the pocket from the first leg;

wherein with the linking element positioned in the pocket and resting against the planar surface of the seat portion, the first projection exerts a provisional clamping force on the linking element for provisionally retaining the linking element within the pocket to restrict axial and/or rotational movement of the linking element relative to the receiver; and a final fastening structure for retaining the linking element in a final position within the pocket, the final fastening structure including a sleeve mounted about an exterior of the first and second legs.

* * * * *